United States Patent
Balcombe

(10) Patent No.: US 12,201,641 B2
(45) Date of Patent: Jan. 21, 2025

(54) **COMPOSITIONS COMPRISING *WITHANIA SOMNIFERA* EXTRACT FOR MAMMALIAN CONSUMPTION**

(71) Applicant: SpecNova LLC, Tysons Corner, VA (US)

(72) Inventor: Sebastian Balcombe, Tysons Corner, VA (US)

(73) Assignee: SPECNOVA LLC, Evergreen, CO (US)

( * ) Notice: Subject to any disclaimer, the term of this patent is extended or adjusted under 35 U.S.C. 154(b) by 0 days.

(21) Appl. No.: 17/808,012

(22) Filed: Jun. 21, 2022

(65) Prior Publication Data
US 2022/0409635 A1    Dec. 29, 2022

Related U.S. Application Data

(60) Provisional application No. 63/212,890, filed on Jun. 21, 2021.

(51) Int. Cl.
| | |
|---|---|
| *A61K 31/585* | (2006.01) |
| *A23L 33/105* | (2016.01) |
| *A61K 31/4025* | (2006.01) |
| *A61K 31/4458* | (2006.01) |
| *A61K 31/454* | (2006.01) |
| *A61K 31/4545* | (2006.01) |
| *A61K 31/7048* | (2006.01) |
| *A61K 36/81* | (2006.01) |
| *A61P 25/28* | (2006.01) |

(52) U.S. Cl.
CPC .......... *A61K 31/585* (2013.01); *A23L 33/105* (2016.08); *A61K 31/4025* (2013.01); *A61K 31/4458* (2013.01); *A61K 31/454* (2013.01); *A61K 31/4545* (2013.01); *A61K 31/7048* (2013.01); *A61K 36/81* (2013.01); *A61P 25/28* (2018.01); *A23V 2002/00* (2013.01); *A61K 2236/15* (2013.01); *A61K 2236/331* (2013.01); *A61K 2236/333* (2013.01); *A61K 2236/51* (2013.01)

(58) Field of Classification Search
CPC .............. A61K 31/585; A61K 31/4025; A61K 31/4458; A61K 31/454; A61K 31/4545; A61K 31/7048; A61K 36/81; A61K 2236/15; A61K 2236/331; A61K 2236/333; A61K 2236/51; A23L 33/105; A61P 25/28; A23V 2002/00
See application file for complete search history.

(56) References Cited

FOREIGN PATENT DOCUMENTS

| WO | WO-2012160569 A1 | * | 11/2012 | ............. A61K 36/81 |
| WO | WO-2020079712 A1 | * | 4/2020 | ........... A23L 33/105 |

* cited by examiner

*Primary Examiner* — Yih-Horng Shiao
*Assistant Examiner* — Hoi Yan Lee
(74) *Attorney, Agent, or Firm* — HESLIN ROTHENBERG FARLEY & MESITI P.C.

(57) ABSTRACT

Provided is a *Withania somnifera* extract composition contains at least one of withaferin A, withanoside IV, withanoside V, withanoside VI, withanolide A, withanolide B, anaferine, anahygrine, 12-deoxywithastromonolide, sitoindoside X, sitoindoside IX, cuscohygrine, isopelletierine, bracteosin A, bracteosin B, or bracteosin C, or a salt or solvate of any one thereof. Related compositions, methods, and processes are also provided.

13 Claims, 4 Drawing Sheets

COMPOSITIONS COMPRISING *WITHANIA SOMNIFERA* EXTRACT FOR MAMMALIAN CONSUMPTION

CROSS REFERENCE TO RELATED APPLICATIONS

This application claims the benefit of U.S. provisional application No. 63/212,890, filed on Jun. 21, 2021, the entire contents of which are hereby incorporated by reference herein.

FIELD OF THE INVENTION

The invention relates to a novel *Withania somnifera* extract composition and to its various uses as a nutraceutical or pharmaceutical composition. The invention also relates to a novel process for preparing the aforementioned composition.

BACKGROUND OF THE INVENTION

*Withania somnifera*, commonly known as Ashwagandha, is a green shrub found throughout the drier parts of India, Pakistan, Afghanistan, Sri Lanka, Congo, South Africa and Egypt. Ashwaganda is commonly used in Ayurveda, a traditional system of medicine practiced in India, and is often used in formulations prescribed for stress, strain, fatigue, pain, skin diseases, diabetes, gastrointestinal disease, rheumatoid arthritis, and epilepsy. It is also employed as a general tonic to improve energy levels, health, and longevity, and topically as an analgesic.

*Withania somnifera* contains many biologically active chemical constituents including alkaloids such as anaferine and anahygrine, and steroidal lactones such as withanolides and withaferins.

There is therefore a need to provide alternative *Withania somnifera* compositions with improved properties.

SUMMARY OF THE INVENTION

According to the first aspect of the invention, there is provided a *Withania somnifera* extract composition comprising at least one of withaferin A, withanoside IV, withanoside V, withanoside VI, withanolide A, withanolide B, anaferine, anahygrine 12-deoxywithastromonolide, sitoindoside X, sitoindoside IX, cuscohygrine, isopelletierine, bracteosin A, bracteosin B, and bracteosin C, or a salt or solvate of any one thereof.

According to a further aspect of the invention there is provided a nutraceutical composition comprising the extract composition as described herein, and one or more nutraceutically acceptable excipients.

According to a further aspect of the invention there is provided a pharmaceutical composition comprising the extract composition as described herein, and one or more pharmaceutically acceptable excipients.

According to a further aspect of the invention there is provided a process for preparing the composition as described herein, which comprises the steps of (a) drying *Withania somnifera* roots and/or leaves; (b) crushing the material obtained in step (a) to obtain a dry powder; (c) extracting the dry powder obtained in step (b) with an aqueous alcohol solvent followed by filtration to obtain the supernatant and residue; (d) subjecting the supernatant obtained in step (c) to distillation to obtain the crude extract; (e) purifying the crude extract obtained in step (d), thereby obtaining the first extract; (f) subjecting the residue obtained in step (c) to hot water extraction followed by filtration and collection of the supernatant to obtain the second extract; and (g) combining the first and second extracts obtained in steps (e) and (f).

DETAILED DESCRIPTION OF THE INVENTION

*Withania somnifera* Extract Composition

Figure 1A:
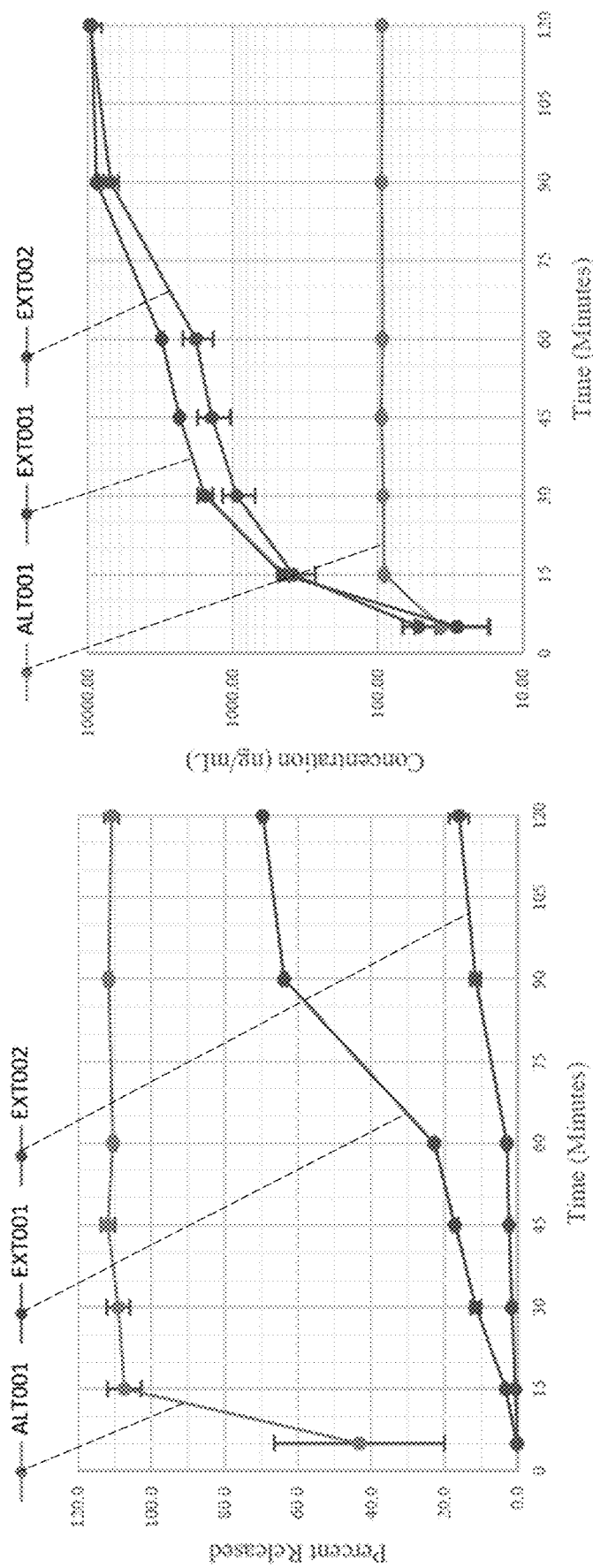
FIGS. 1A-D: Results of dissolution studies showing (left) percent released based on quantitation data over time and (right) concentration over time (A) for withaferin A, (B) withanolide A, (C) withanoside IV, and (D) withanoside V.

According to the first aspect of the invention, there is provided a *Withania somnifera* extract composition comprising at least one of withaferin A, withanoside IV, withanoside V, withanoside VI, withanolide A, withanolide B, anaferine, anahygrine 12-deoxywithastromonolide, sitoindoside X, sitoindoside IX, cuscohygrine, isopelletierine, bracteosin A, bracteosin B, and bracteosin C, or a salt or solvate of any one thereof.

References herein to "withaferin A" refer to a compound having the following structure:

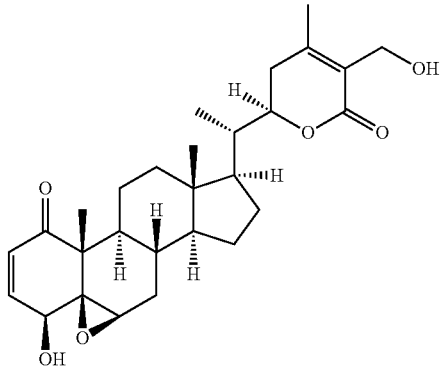

or a salt or solvate thereof.

References herein to "withanoside IV" refer to a compound having the following structure:

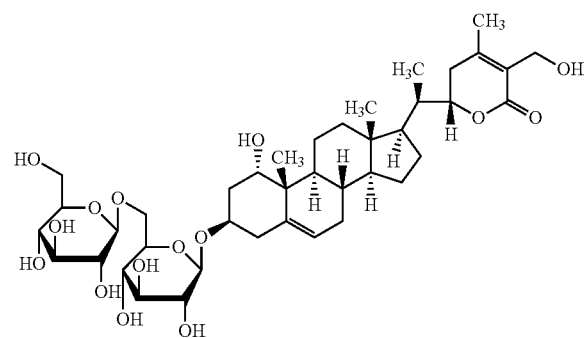

or a salt or solvate thereof.

References herein to "withanoside V" refer to a compound having the following structure:

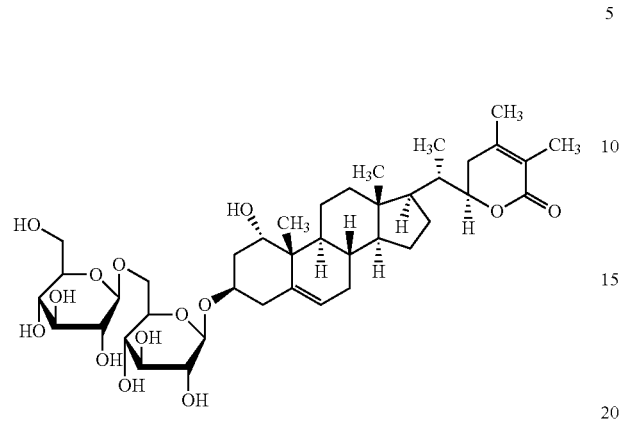

or a salt or solvate thereof.

References herein to "withanoside VI" refer to a compound having the following structure:

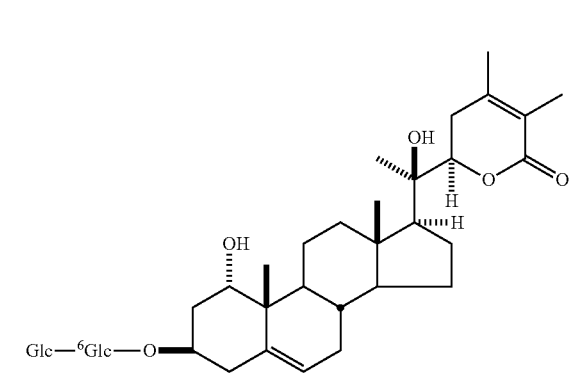

or a salt or solvate thereof.

References herein to "withanolide A" refer to a compound having the following structure:

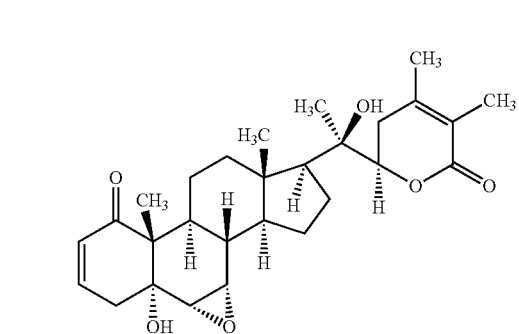

or a salt or solvate thereof.

References herein to "withanolide B" refer to a compound having the following structure:

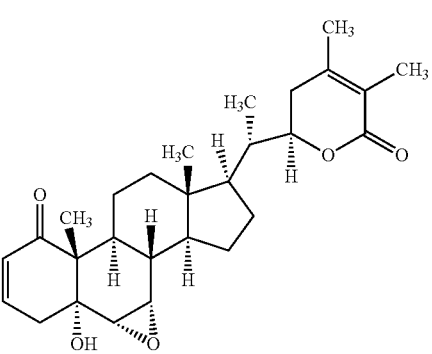

or a salt or solvate thereof.

References herein to "anaferine" refer to a compound having the following structure:

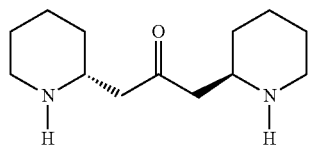 [SMILES: O=C(C[C@H]1CCCCN1)C[C@H]1CCCCN1]

or a salt or solvate thereof.

References herein to "anahygrine" refer to a compound having the following structure:

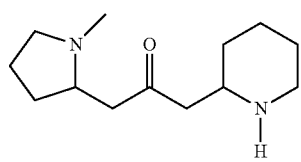 [SMILES: CN1CCCC1CC(=O)CC1CCCCN1]

or a salt or solvate thereof.

References herein to "12-deoxywithastromonolide" refer to a compound having the following structure:

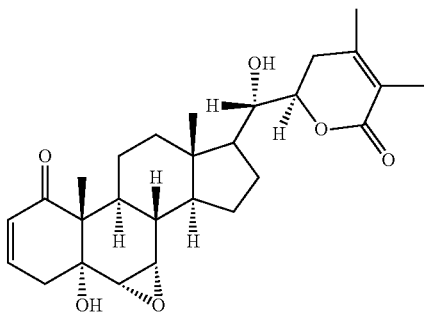

or a salt or solvate thereof.

References herein to "sitoindoside X" refer to a compound having the following structure:

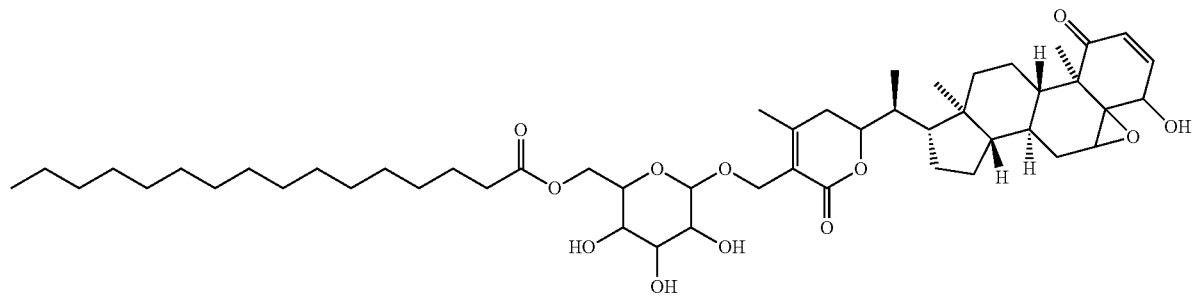 [SMILES: CCCCCCCCCCCCCCCC(=O)OCC1OC(OCC2=C(C)CC([C@@H](C)[C@H]3CC[C@H]4[C@@H]5CC6OC67C(O)C=CC(=O)[C@]7(C)[C@H]5CC[C@]34C)OC2=O)C(O)C(O)C1O]

or a salt or solvate thereof.

References herein to "sitoindoside IX" refer to a compound having the following structure:

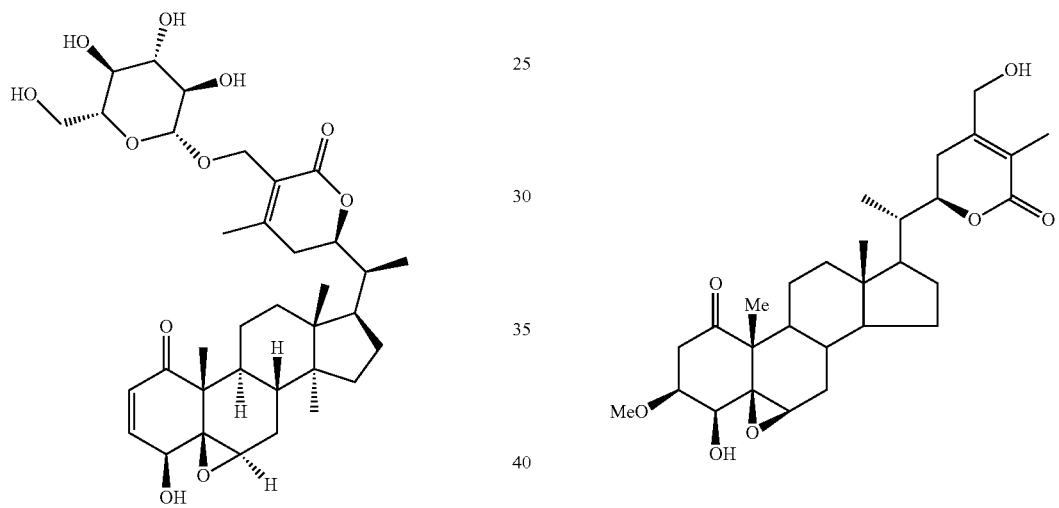

or a salt or solvate thereof.

References herein to "cuscohygrine" refer to a compound having the following structure:

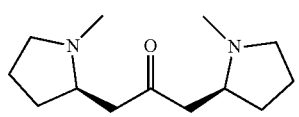 [SMILES: CN1CCC[C@@H]1CC(=O)C[C@@H]1CCCN1C]

or a salt or solvate thereof.

References herein to "isopelletierine" refer to a compound having the following structure:

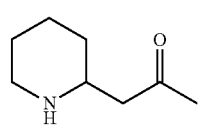

or a salt or solvate thereof.

References herein to "bracteosin A" refer to a compound having the following structure:

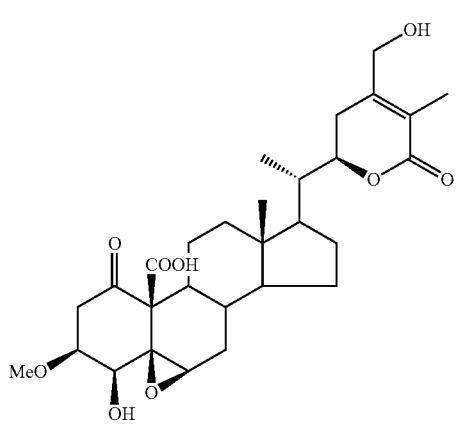 [SMILES: CO[C@H]1CC(=O)[C@]2(C(=O)O)C3CC[C@@]4(C)C(CCC4[C@H](C)[C@H]4CC(CO)=C(C)C(=O)O4)C3C[C@H]3O[C@]32[C@H]1O]

or a salt or solvate thereof.

References herein to "bracteosin B" refer to a compound having the following structure:

or a salt or solvate thereof.

References herein to "bracteosin C" refer to a compound having the following structure:

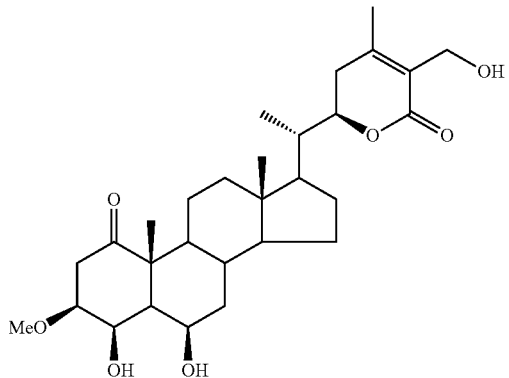 [SMILES: CO[C@H]1CC(=O)[C@]2(C)C3CC[C@@]4(C)C(CCC4[C@H](C)[C@H]4CC(C)=C(CO)C(=O)O4)C3C[C@@H](O)C2[C@H]1O]

or a salt or solvate thereof.

In one embodiment, the composition comprises at least two of withaferin A, withanoside IV, withanoside V, withanoside VI, withanolide A, withanolide B, anaferine, anahygrine 12-deoxywithastromonolide, sitoindoside X, sitoindoside IX, cuscohygrine, isopelletierine, bracteosin A, bracteosin B, and bracteosin C, or a salt or solvate of any one thereof.

In one embodiment, the composition comprises at least three of withaferin A, withanoside IV, withanoside V, withanoside VI, withanolide A, withanolide B, anaferine, anahygrine 12-deoxywithastromonolide, sitoindoside X, sitoindoside IX, cuscohygrine, isopelletierine, bracteosin A, bracteosin B, and bracteosin C, or a salt or solvate of any one thereof.

In one embodiment, the composition comprises at least four of withaferin A, withanoside IV, withanoside V, withanoside VI, withanolide A, withanolide B, anaferine, anahygrine 12-deoxywithastromonolide, sitoindoside X, sitoindoside IX, cuscohygrine, isopelletierine, bracteosin A, bracteosin B, and bracteosin C, or a salt or solvate of any one thereof.

In one embodiment, the composition comprises at least five of withaferin A, withanoside IV, withanoside V, withanoside VI, withanolide A, withanolide B, anaferine, anahygrine 12-deoxywithastromonolide, sitoindoside X, sitoindoside IX, cuscohygrine, isopelletierine, bracteosin A, bracteosin B, and bracteosin C, or a salt or solvate of any one thereof.

In one embodiment, the composition comprises at least six of withaferin A, withanoside IV, withanoside V, withanoside VI, withanolide A, withanolide B, anaferine, anahygrine 12-deoxywithastromonolide, sitoindoside X, sitoindoside IX, cuscohygrine, isopelletierine, bracteosin A, bracteosin B, and bracteosin C, or a salt or solvate of any one thereof.

In one embodiment, the composition comprises at least seven of withaferin A, withanoside IV, withanoside V, withanoside VI, withanolide A, withanolide B, anaferine, anahygrine 12-deoxywithastromonolide, sitoindoside X, sitoindoside IX, cuscohygrine, isopelletierine, bracteosin A, bracteosin B, and bracteosin C, or a salt or solvate of any one thereof.

In one embodiment, the composition comprises at least eight of withaferin A, withanoside IV, withanoside V, withanoside VI, withanolide A, withanolide B, anaferine, anahygrine 12-deoxywithastromonolide, sitoindoside X, sitoindoside IX, cuscohygrine, isopelletierine, bracteosin A, bracteosin B, and bracteosin C, or a salt or solvate of any one thereof.

In one embodiment, the composition comprises at least nine of withaferin A, withanoside IV, withanoside V, withanoside VI, withanolide A, withanolide B, anaferine, anahygrine 12-deoxywithastromonolide, sitoindoside X, sitoindoside IX, cuscohygrine, isopelletierine, bracteosin A, bracteosin B, and bracteosin C, or a salt or solvate of any one thereof.

In one embodiment, the composition comprises at least ten of withaferin A, withanoside IV, withanoside V, withanoside VI, withanolide A, withanolide B, anaferine, anahygrine 12-deoxywithastromonolide, sitoindoside X, sitoindoside IX, cuscohygrine, isopelletierine, bracteosin A, bracteosin B, and bracteosin C, or a salt or solvate of any one thereof.

In one embodiment, the composition comprises at least eleven of withaferin A, withanoside IV, withanoside V, withanoside VI, withanolide A, withanolide B, anaferine, anahygrine 12-deoxywithastromonolide, sitoindoside X, sitoindoside IX, cuscohygrine, isopelletierine, bracteosin A, bracteosin B, and bracteosin C, or a salt or solvate of any one thereof.

In one embodiment, the composition comprises at least twelve of withaferin A, withanoside IV, withanoside V, withanoside VI, withanolide A, withanolide B, anaferine, anahygrine 12-deoxywithastromonolide, sitoindoside X, sitoindoside IX, cuscohygrine, isopelletierine, bracteosin A, bracteosin B, and bracteosin C, or a salt or solvate of any one thereof.

In one embodiment, the composition comprises at least thirteen of withaferin A, withanoside IV, withanoside V, withanoside VI, withanolide A, withanolide B, anaferine, anahygrine, 12-deoxywithastromonolide, sitoindoside X, sitoindoside IX, cuscohygrine, isopelletierine, bracteosin A, bracteosin B, and bracteosin C, or a salt or solvate of any one thereof.

In one embodiment, the composition comprises at least fourteen of withaferin A, withanoside IV, withanoside V, withanoside VI, withanolide A, withanolide B, anaferine, anahygrine and 12-deoxywithastromonolide, sitoindoside X, sitoindoside IX, cuscohygrine, isopelletierine, bracteosin A, bracteosin B, bracteosin C, or a salt or solvate of any one thereof.

In one embodiment, the composition comprises at least fifteen of withaferin A, withanoside IV, withanoside V, withanoside VI, withanolide A, withanolide B, anaferine, anahygrine, 12-deoxywithastromonolide, sitoindoside X, sitoindoside IX, cuscohygrine, isopelletierine, bracteosin A, bracteosin B, and bracteosin C, or a salt or solvate of any one thereof.

In one embodiment, the composition comprises each of withaferin A, withanoside IV, withanoside V, withanoside VI, withanolide A, withanolide B, anaferine, anahygrine and 12-deoxywithastromonolide, sitoindoside X, sitoindoside IX, cuscohygrine, isopelletierine, bracteosin A, bracteosin B, bracteosin C, or a salt or solvate of any one thereof.

In one embodiment, the composition comprises withanoside IV, withanoside V, withanoside VI and withanolide A, or a salt or solvate of any one thereof.

In a further embodiment, the composition comprises withaferin A, withanolide A, withanoside IV and withanoside V, or a salt or solvate of any one thereof.

In one embodiment, the withanolides comprise at least 3% (w/w) of said composition.

In one embodiment, withaferin A comprises at least 2% (w/w) of said composition. In a further embodiment, withaferin A comprises between 2% (w/w) and 11% (w/w) of said composition, such as 2.462% (w/w) or 10.736% (w/w).

In one embodiment, withanolide A comprises at least 0.02% (w/w) of said composition. In a further embodiment, withanolide A comprises between 0.02% (w/w) and 0.2% (w/w) of said composition, such as 0.024% (w/w) or 0.120% (w/w).

In one embodiment, withanoside IV comprises at least 0.05% (w/w) of said composition. In a further embodiment, withanoside IV comprises between 0.05% (w/w) and 0.4% (w/w) of said composition, such as 0.065% (w/w) or 0.329% (w/w).

In one embodiment, withanoside V comprises at least 0.5% (w/w) of said composition. In a further embodiment, withanoside V comprises between 0.5% (w/w) and 4% (w/w) of said composition, such as 0.587% (w/w) or 3.094% (w/w).

In one embodiment, the composition comprises:
at least 2% (w/w) of withaferin A, such as between 2% (w/w) and 11% (w/w) of withaferin A, in particular 2.462% (w/w) or 10.736% (w/w); and
at least 0.02% (w/w) of withanolide A, such as between 0.02% (w/w) and 0.2% (w/w), in particular 0.024% (w/w) or 0.120% (w/w); and
at least 0.02% (w/w) of withanoside IV, such as between 0.05% (w/w) and 0.4% (w/w), in particular 0.024% (w/w) or 0.120% (w/w); and
at least 0.5% (w/w) of withanoside V, such as between 0.5% (w/w) and 4% (w/w), in particular 0.587% (w/w) or 3.094% (w/w).

References to compounds of the invention also include ionic forms, salts, solvates, isomers (including geometric and stereochemical isomers), tautomers, esters, prodrugs, isotopes and protected forms thereof, for example, as discussed below; preferably, the salts or tautomers or isomers or solvates thereof; and more preferably, the salts or tautomers or solvates thereof, even more preferably the salts or tautomers or solvates thereof. Hereinafter, compounds and their ionic forms, salts, solvates, isomers (including geometric and stereochemical isomers), tautomers, esters, prodrugs, isotopes and protected forms thereof as defined in any aspect of the invention (except intermediate compounds in chemical processes) are referred to as "compounds of the invention".

Salts

Certain compounds of the invention can exist in the form of salts, for example acid addition salts or, in certain cases salts of organic and inorganic bases such as carboxylate, sulfonate and phosphate salts. All such salts are within the scope of this invention, and references to compounds of the invention include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, non-aqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

The compounds of the invention may exist as mono- or di-salts depending upon the $pK_a$ of the acid from which the salt is formed.

It will be appreciated that for use in medicine the salts of the compounds of the invention should be pharmaceutically acceptable. Suitable pharmaceutically acceptable salts will be apparent to those skilled in the art. Pharmaceutically acceptable salts include those described by Berge, Bighley and Monkhouse, *J. Pharm. Sci.* 1977, 66, pp. 1-19. Such pharmaceutically acceptable salts include acid addition salts formed with inorganic acids e.g. hydrochloric, hydrobromic, sulfuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates may be used, for example in the isolation of compounds of the invention and are included within the scope of this invention. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Certain of the compounds of the invention may form acid addition salts with one or more equivalents of the acid. The present invention includes within its scope all possible stoichiometric and non-stoichiometric forms.

Solvates

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compounds of the invention are within the scope of the invention. In one embodiment, the pharmaceutically acceptable solvates of the compounds of the invention include the hydrate thereof.

Prodrugs

It will be appreciated by those skilled in the art that certain protected derivatives of compounds of the invention, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of pro-drug functionality suitable for the compounds of the present invention are described in *Drugs of Today*, 19, 9, 1983, 499-538 and in *Topics in Chemistry*, Chapter 31, pp. 306-316 and in "*Design of Prodrugs*" by H. Bundgaard, Elsevier, 1985, Chapter 1. It will further be appreciated by those skilled in the art, that certain moieties, known to those skilled in the art as "pro-moieties", for example as described by H. Bundgaard in "*Design of Prodrugs*" may be placed on appropriate functionalities when such functionalities are present within compounds of the invention.

Certain specific examples of pro-drugs include sulphonated, glucuronidated, methylated, esterificated, acetylated, glutathionated and glycine conjugated derivatives of the compounds of the invention.

Also included within the scope of the compounds and various salts of the invention are polymorphs thereof.

Enantiomers

Where chiral centres are present in compounds of the invention, the present invention includes within its scope all possible enantiomers and diastereoisomers, including mixtures thereof. The different isomeric forms may be separated or resolved one from the other by conventional methods, or any given isomer may be obtained by conventional synthetic methods or by stereospecific or asymmetric syntheses. The invention also extends to any tautomeric forms or mixtures thereof.

Isotopes

The subject invention also includes all pharmaceutically acceptable isotopically-labelled compounds which are identical to those recited in the compounds of the invention but for the fact that one or more atoms are replaced by an atom having an atomic mass or mass number different from the atomic mass or mass number most commonly found in nature.

Examples of isotopes suitable for inclusion in the compounds of the invention comprise isotopes of hydrogen, such as $^2H$ (D) and $^3H$ (T), carbon, such as $^{11}C$, $^{13}C$ and $^{14}C$, chlorine, such as $^{36}Cl$, fluorine, such as $^{18}F$, iodine, such as $^{123}I$, $^{125}I$ and $^{131}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Certain isotopically-labelled compounds of the invention, for example, those incorporating a radioactive isotope, are useful in drug and/or substrate tissue distribution studies. The compounds of the invention can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase) etc. The radioactive isotopes tritium, i.e. $^3H$ (T), and carbon-14, i.e. $^{14}C$, are particularly useful for this purpose in view of their ease of incorporation and ready means of detection.

Substitution with heavier isotopes such as deuterium, i.e. $^2H$ (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining target occupancy.

Isotopically-labelled compounds of the invention can generally be prepared by conventional techniques known to those skilled in the art using appropriate isotopically-labelled reagents in place of the non-labelled reagent previously employed.

Purity

Since the compounds of the invention are each preferably provided in substantially pure form, for example at least 60% pure, more suitably at least 75% pure and preferably at least 85%, especially at least 98% pure (% are given on a weight for weight basis). Impure preparations of the compounds may be used for preparing the more pure forms used in the composition.

Nutraceutical Compositions

References herein to a nutraceutical refer to a food, food product, food additive or dietary supplement that provides health and/or medical benefits, such as preventing, treating and enhancing mammalian (e.g. human) conditions. References herein to food extend equally to a drink or beverage comprising said nutraceutical.

According to a further aspect of the invention there is provided a nutraceutical composition comprising the extract composition as described herein, and one or more nutraceutically acceptable excipients.

In one embodiment, the nutraceutical composition additionally comprises one or more additional active ingredients.

In one embodiment, the nutraceutical composition is a tablet or capsule.

In one embodiment, the nutraceutical composition is a food or beverage selected from: water, milk, coffee, tea, juice, protein shake, energy drink, yoghurt and cereal or chocolate bar.

In one embodiment, the nutraceutical composition is for use as a food, food product, food additive or dietary supplement.

The nutraceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of nutraceutical compositions are set out in more detail below.

The term "nutraceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Nutraceutical compositions containing compounds of the invention can be formulated in accordance with known techniques, see for example, Remington's Pharmaceutical Sciences, Mack Publishing Company, Easton, PA, USA.

The nutraceutical compositions can be administered to the subject in need thereof in any suitable and convenient form. Suitably, said administration will be orally or topically.

Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like.

Nutraceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

Tablets may be designed to release the active compound either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the active compound can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compounds of the invention may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. Aug. 1, (2006) 5, 1909.

The nutraceutical compositions typically comprise from approximately 1% (w/w) to approximately 95% (w/w) active ingredient and from 99% (w/w) to 5% (w/w) of a nutraceutically acceptable excipient or combination of excipients. Particularly, the compositions comprise from approximately 20% (w/w) to approximately 90%,% (w/w) active ingredient and from 80% (w/w) to 10% of a nutraceutically acceptable excipient or combination of excipients. The nutraceutical compositions comprise from approximately 1% to approximately 95%, particularly from approximately 20% to approximately 90%, active ingredient.

The nutraceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Nutraceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

Compositions for topical use and nasal delivery include ointments, creams, sprays, patches, gels, liquid drops and inserts (for example intraocular inserts). Such compositions can be formulated in accordance with known methods.

The compounds of the invention will generally be presented in unit dosage form and, as such, will typically contain sufficient compound to provide a desired level of activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired effect.

Although it is anticipated that the nutraceutical composition of the invention will be present within a tablet or capsule, it may also be within a food or beverage. Examples of suitable foods or beverages where the nutraceutical compositions may be contained within include: water, milk, coffee, tea, juice, protein shake, energy drink, yoghurt, cereal or chocolate bar, and the like.

Nutraceutical Utility

According to a further aspect of the invention there is provided the nutraceutical composition as described herein for use in: improving or increasing one or more of the following: mood, self-confidence, relaxation, wakefulness, mental alertness, focus, attention, mental energy, physical energy, natural energy, concentration, reasoning, motivation, stamina, strength, workout output, mobility, athletic speed, reaction time, athletic endurance, alertness, decision making, memory, cognitive performance, verbal fluency, sensuous perception, sexual desire and well being; or reduction of one or more of the following: appetite, boredom, anxiety and fatigue.

Pharmaceutical Compositions

According to a further aspect of the invention there is provided a pharmaceutical composition comprising the extract composition as described herein, and one or more pharmaceutically acceptable excipients.

In one embodiment, the pharmaceutical composition additionally comprises one or more additional active ingredients.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the invention can be formulated in accordance with known techniques, see for example, Remington's Pharmaceutical Sciences, Mack Publishing Company, Easton, PA, USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use. In one embodiment, the formulation is provided as an active pharmaceutical ingredient in a bottle for subsequent reconstitution using an appropriate diluent.

The pharmaceutical formulation can be prepared by lyophilising a compound of the invention. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use.

Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like.

Prolonged absorption of the injectable pharmaceutical form may be brought about by the inclusion of agents which delay absorption such as aluminum monostearate and gelatin.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

Tablets may be designed to release the drug either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compounds of the invention may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. Aug. 1, (2006) 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Particularly, the compositions comprise from approximately 20% (w/w) to approximately 90%, % (w/w) active ingredient and from 80% (w/w) to 10% of a pharmaceutically acceptable excipient or combination of excipients. The pharmaceutical compositions comprise from approximately 1% to approximately 95%, particularly from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the invention will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Therapeutic Utility

According to a further aspect of the invention, there is provided the pharmaceutical composition as defined herein, for use in therapy.

According to a further aspect of the invention there is provided the pharmaceutical composition as defined herein, for use in the prophylaxis or treatment of one or more of the following: attention deficit hyperactivity disorder (ADHD), or stress.

Process

According to a further aspect of the invention there is provided a process for preparing the composition as described herein, which comprises the steps of (a) drying *Withania somnifera* roots and/or leaves; (b) crushing the material obtained in step (a) to obtain a dry powder; (c) extracting the dry powder obtained in step (b) with an aqueous alcohol solvent followed by filtration to obtain the supernatant and residue; (d) subjecting the supernatant obtained in step (c) to distillation to obtain the crude extract; (e) purifying the crude extract obtained in step (d), thereby obtaining the first extract; (f) subjecting the residue obtained in step (c) to hot water extraction followed by filtration and collection of the supernatant to obtain the second extract; and (g) combining the first and second extracts obtained in steps (e) and (f).

In one embodiment, the combined extracts of step (g) are spray dried to obtain an extract powder.

In one embodiment, the drying temperature of step (a) is between 35 and 75° C.

In one embodiment, the aqueous alcohol solvent is ethyl alcohol.

In one embodiment, the temperature of the aqueous alcohol solvent is between 50 and 60° C.

In one embodiment, the purification of step (e) is performed by any one of (i) solvent extraction, (ii) adsorbent resin treatment or (iii) precipitation.

In one embodiment, the purification is performed by solvent extraction. In a further embodiment the solvent is an ethyl acetate/ethyl alcohol mixture.

In one embodiment, the purification is performed by adsorbent resin treatment. In a further embodiment the resin is HP20 resin. In a further embodiment the extract is eluted with ethyl alcohol.

In one embodiment, the purification is performed by precipitation. In a further embodiment the precipitant is sodium chloride.

In one embodiment, the hot water extraction is performed at a temperature of between 65 and 75° C.

The invention will now be described with reference to the following non-limiting examples:

Example 1: Extraction of *Withania somnifera* Roots and/or Leaves

10 Kg of *Withania somnifera* roots and/or leaves were collected. The roots and/or leaves were cleaned by water. The roots and/or leaves were then dried at 37-75° C. for 8 hours/days and crushed to obtain a dry powder. The dry powder was then extracted by adding 120 L ethyl alcohol to the dry powder, and heating to 50-60° C. for 4 hours. The mixture was then filtered to obtain the supernatant and residue. The extraction process was repeated on the obtained residue a further 2 times. The obtained supernatants were combined and distilled to obtain the crude extract.

Example 2: Solvent Extraction of the Crude Extract

7 Kg of crude extract was dispersed in 35 Kg of ethyl acetate/ethyl alcohol 90:10 (v/v). The mixture was stirred for 10 minutes and then left at 20-25° C. for 5 hours. The mixture was then filtered to obtain the supernatant and residue, and the supernatant was concentrated to remove all solvent. The yield of first extract from the crude extract was 50-65%. The total withanolide content was 10-12% as measured by HPLC.

Example 3: Adsorbent Resin Treatment of the Crude Extract

7 Kg of crude extract was made into a slurry with 30 L of water and passed through HP 20 resin. The resin was washed with 200 mL of ethyl alcohol/water 50:50 (v/v) and the eluent collected. The eluent was concentrated to remove solvent completely to obtain the first extract. The yield of first extract from the crude extract was 40-50%. The total withanolide content was 15-18% as measured by HPLC.

Example 4: Precipitation of the Crude Extract

7 Kg of crude extract was dissolved in 50 L of water. 8-10 Kg of sodium chloride was then dissolved into the mixture to obtain a saturated solution. The mixture was then filtered to obtain the supernatant and residue. The obtained supernatant was distilled to obtain the first extract.

Example 5: Preparation of the Second Extract

The residue obtained from the ethyl alcohol extraction (see Example 1) was further extracted using water at a 1:10 ratio of residue:water (5 Kg:50 L) at a temperature of 65-75° C. for 3 hours. The mixture was then filtered to obtain the supernatant and residue. The extraction process was repeated on the obtained residue. The obtained supernatants were pooled to obtain the second extract.

Example 6: HPLC Analysis of the *Withania somnifera* Extract

The first and second extracts (see Examples 2-5) were combined to obtain the *Withania somnifera* extract and concentrated to a quarter of the starting volume. The resulting extract was analysed by HPLC.

Example 7: Spray Drying of the *Withania somnifera* Extract

The *Withania somnifera* extract (see Example 6) was spray dried with an inlet air temperature of 160-230° C., an outlet air temperature of 60-100° C., and an atomization pressure of 294-588 kPa.

Example 8: Quantification of Withanolides in the *Withania somnifera* Extract

The withanolide concentrations of two *Withania somnifera* extracts prepared by the claimed method of the present application (EXT001 and EXT002) and one *Withania somnifera* extract prepared using an alternative method (ALT001) were measured for comparison. Each of the extract powders were accurately weighed (200±5 mg; N=2, each) and dissolved in 40 mL of methanol to make a 5 mg/mL mixture. The mixtures were vortex mixed for 8 minutes, sonicated for 10 minutes, vortex mixed again for 5 minutes, sonicated 10 minutes, vortex mixed for one minute, and then centrifuged at 2100 RPM for two minutes. The supernatant of the mixtures was then diluted in two steps with 50:50 water:acetonitrile to make both 50 and 20 µg/mL mixtures of total volume 250 µL with 50 ng/mL mitragynine internal standard (IS). The mixtures were then centrifuge filtered in a 96-well plate for 2 minutes at 2100 RPM into a 96-well 700 µL UPLC plate and sealed. The samples were assayed along with calibration and quality control standards using UPLC-MS/MS system.

The percent w/w and concentrations of each withanolide in the three *Withania somnifera* extracts are shown in the following table:

TABLE 1

Percent w/w and concentrations (mg/g) of withanolides
in three *Withania Somnifera* extracts

| Withanolide | | ALT001 | EXT001 | EXT002 |
| --- | --- | --- | --- | --- |
| Withaferin A | % w/w | 0.014% | 2.462% | 10.736% |
| | (mg/g) | (0.14 ± 0.02 mg) | (24.62 ± 0.66 mg) | (107.36 ± 0.23 mg) |
| Withanolide A | % w/w | 0.050% | 0.024% | 0.120% |
| | (mg/g) | (0.50 ± 0.04 mg) | (0.24 ± 0.03 mg) | (1.20 ± 0.13 mg) |
| Withanoside IV | % w/w | 0.0115% | 0.065% | 0.329% |
| | (mg/g) | (0.115 ± 0.004 mg) | (0.65 ± 0.04 mg) | (3.29 ± 0.24 mg) |
| Withanoside V | % w/w | 0.016% | 0.587% | 3.094% |
| | (mg/g) | (0.16 ± 0.02 mg) | (5.87 ± 0.49 mg) | (30.94 ± 0.06 mg) |

Example 9: Withanolide Dissolution of the *Withania somnifera* Extract

The dissolution of withanolides within two *Withania somnifera* extracts prepared by the claimed method of the present application (EXT001 and EXT002) and one *Withania somnifera* extract prepared using an alternative method (ALT001) was measured for comparison. 900 mL of 10 mM potassium phosphate buffer (pH=7.41) buffer was added to each of six wells of the dissolution apparatus (Type 2, paddle). Size 00 capsules were filled with ~500 mg of each of the three *Withania somnifera* extracts (N=2, each). The temperature of the dissolution apparatus was set to 37° C. and the rotation speed to 75 RPM. Capsules were fitted in sinkers and then dropped into each of the 6 wells of the apparatus. 1 mL aliquots were taken for each sample at time points: 5, 15, 30, 45, 60, 90, and 120 minutes. After each draw, 1 mL of buffer was replaced into the wells. The samples were then centrifuge filtered at 2100 RPM for 2 minutes and stored at 4° C. until analysis.

112.5 µL of each sample was added to 112.5 µL of acetonitrile and 25 µL of Mitragynine internal standard (IS) (final concentration of IS=50 ng/µL). The samples were then centrifuge filtered in a 96-well plate at 2100 RPM for 2 minutes into a 96-well 700 µL UPLC plate and sealed. The samples were assayed along with freshly prepared calibration and quality control standards using UPLC-MS/MS system.

Figure 1B:
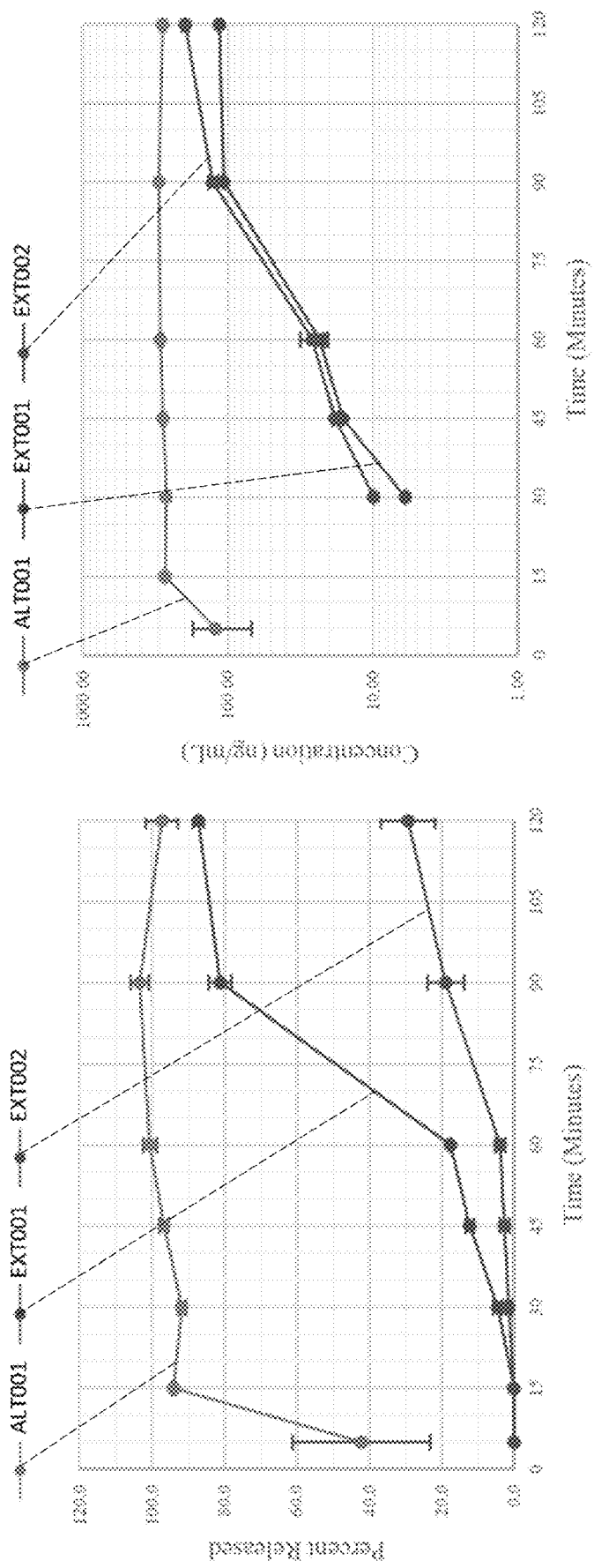
Figure 1C:
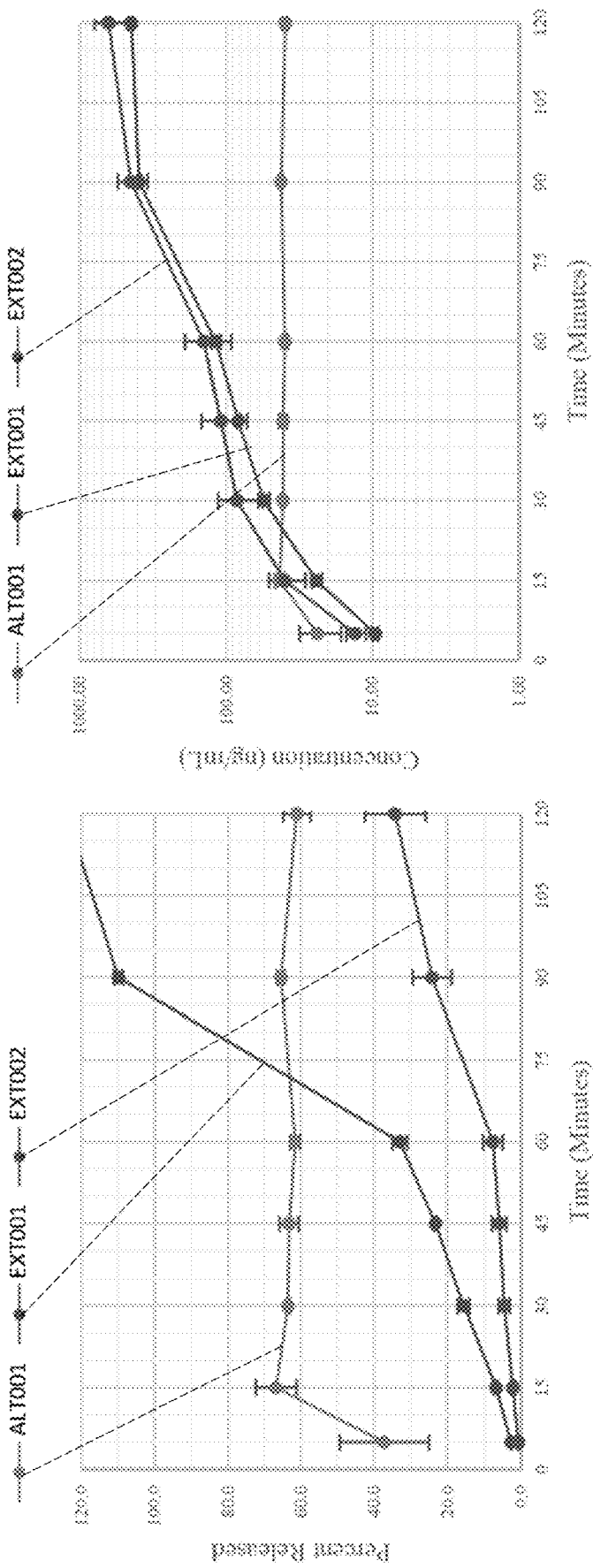
Figure 1D:
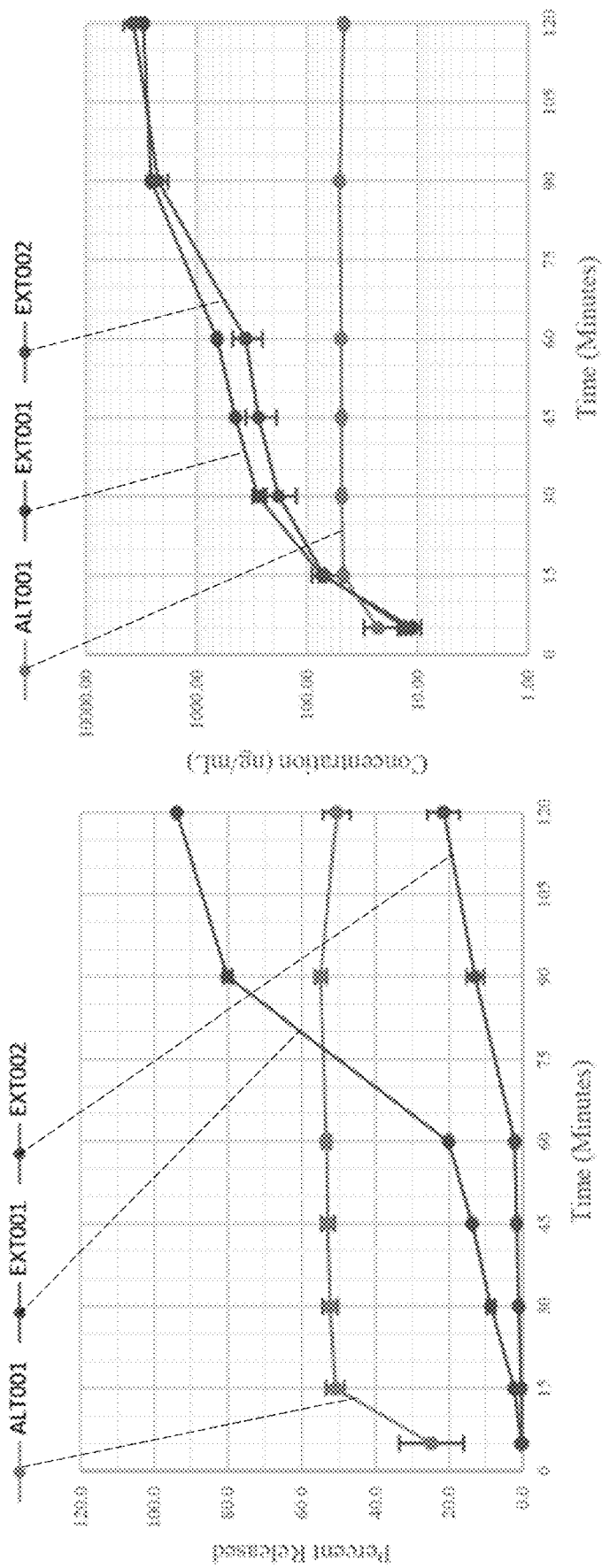

Data is presented herein which exemplifies the dissolution over time of withaferin A, withanolide A, withanoside IV, and withanoside V in each of the three *Withania somnifera* extracts (FIGS. 1A-D).

Example 10: Caco-2 Permeability Assessment of the *Withania somnifera* Extract The Caco-2 permeability of two *Withania somnifera* extracts prepared by the claimed method of the present application (EXT001 and EXT002) and one *Withania somnifera* extract prepared using an alternative method (ALT001) were measured for comparison. Caco-2 cells (ATCC HTB-37) were grown on 24 well Transwell plates for 21 days. as per internal protocol number MET-TDDC-011. On the day of experiment the transepithelial electrical resistance (TEER) was measured across the monolayer and wells with TEER greater than 200 ohm*cm² were used for the permeability assessment. Incubation buffer consisted of Hanks balanced salt solution (HBSS) without $CaCl_2$ and $MgCl_2$, adjusted to pH 7.4, for both the donor and the receiver. Chlorothiazide was used as low permeability reference while caffeine was used as high permeability references in the assay. Lucifer yellow was used as zero permeability reference to check membrane integrity.

The compound solutions were prepared in HBSS buffer (pH 7.4) at a concentration of 1 µg/mL for permeability assessment. 5 mg each of *Withania somnifera* extracts EXT002 and EXT001 were added to 5 mL of HBSS buffer and vortexed for 2 hours followed by filtration through 0.22 µm syringe filter. These solutions were used for permeability determination. Due to low total withanolide content, 1 g of Ashwagandha product ALT001 was added to 10 mL methanol and vortex mixed for 5 min followed by sonication for 10 min and vortex mixed again for 5 min. The methanolic extract was filtered through 0.22 µm filter. This extract was concentrated to 1 mL by passing nitrogen gas at 40° C. for 1 hr. Then 20 µL of this extract was spiked in 2 mL of HBSS buffer and filtered through 0.22 µm filter. This solution was used for the permeability study. Reference compounds caffeine (high permeability) and chlorothiazide (low permeability) were prepared at a concentration of 5 µg/mL in HBSS buffer.

The permeability assay was performed in triplicate for each compound or product. Prior to the permeability assay, the transwells were washed with in pre-warmed HBSS buffer. The medium in the insert was aspirated and then the transwells were transferred to a 24-well plate with blank HBSS buffer (600 µL) in each well, and compound solution (102.5 µL, of which 2.5 µL was sampled immediately as the zero-minute donor) was added to each insert. Receiver samples (25 µL) were collected at 60, and 120 minutes, and replaced with an equal volume of fresh pre-warmed receiver buffer (at 60 minutes). The donor side was sampled (2.5 µL) at 0 and 120 minutes. The assay was conducted at 37° C. in a humidified CO2 incubator.

For analysis, any necessary dilutions of samples were performed with HBSS, pH 7.4. 25 µL of sample was mixed with 100 µL of acetonitrile with 25 ng/mL of mitragynine internal standard (IS), and then mixed and filtered through 0.4 µm filter plate to by centrifugation for 5 minutes at 2,000 rpm to a polypropylene 96-well plate for analysis. The samples were assayed by LC-MS/MS method.

The apparent permeability coefficient ($P_{app}$) and recovery were calculated as follows:

$$P_{app} = \left(\frac{V_A}{A*T}\right) * \left(\frac{[\text{Drug}]_{acceptor}}{[\text{Drug}]_{ini,donor}}\right)$$

Where, VA is the volume of the acceptor compartment; A is the diffusional area of the membrane (0.33 cm²); T is the length of study; $[\text{Drug}]_{ini,donor}$ is the donor compound amount at 0 minute; $[\text{Drug}]_{acceptor}$ is the acceptor compound amount at 120 minute. The compounds with permeability above $5×10^{-6}$ cm/s will be considered high permeability compounds while those with permeability below $5×10^{-6}$ cm/s will be considered low permeability compounds.

Unidirectional permeation assessment for the test articles across Caco-2 monolayer was conducted as described above, with chlorothiazide (low-permeability reference compound) and caffeine (high permeability reference compound) run in parallel to the test compounds.

The unidirectional permeability of the three *Withania somnifera* extracts across a Caco-2 cell monolayer are shown in the following table:

TABLE 2

Unidirectional permeability across Caco-2 cell monolayer (pH.7.4)

| Compound/Extract | | Caco-2 Permeability ($P_{app}$) (*$10^{-6}$ cm/sec) (A→B) | Permeability Class |
|---|---|---|---|
| Caffeine | | 25.25 ± 0.43 | High |
| Chlorothiazide | | 4.20 ± 1.79 | Low |
| Alone$ | Withaferin A | 4.55 ± 0.81 | Low |
| | Withanolide A | 3.23 ± 0.50 | Low |
| | Withanoside IV | 5.42 ± 0.69 | High |
| | Withanolside V | 4.03 ± 0.87 | Low |
| ALT001# | Withaferin A | 2.37 ± 0.16 | Low |
| | Withanolide A | 8.50 ± 0.63 | High |
| | Withanoside IV | 4.77 ± 0.25 | Low |
| | Withanolside V | 4.38 ± 1.03 | Low |
| EXT001@ | Withaferin A | 0.85 ± 0.11 | Low |
| | Withanolide A | 10.26 ± 1.61 | High |
| | Withanoside IV | 4.85 ± 0.73 | Low |
| | Withanolside V | 3.85 ± 0.46 | Low |
| EXT002@ | Withaferin A | 0.89 ± 0.28 | Low |
| | Withanolide A | 9.57 ± 2.57 | High |
| | Withanoside IV | 2.89 ± 0.42 | Low |
| | Withanolside V | 2.49 ± 0.11 | Low |

$Performed at 1 µg/mL concentration for each compound
1 g of *Withania Somnifera* extract ALT001 was added to 10 mL methanol for extraction and concentrated to 1 mL after filtration. Then 20 µL of this extract was spiked in 2 mL of HBSS buffer.
@5 mg of *Withania Somnifera* extract was added to 5 mL HBSS buffer.

Example 11: Improvement of Cognitive Function with *Withania somnifera* Extract

The effect of a *Withania somnifera* extract composition prepared by the claimed method of the present application on cognitive function was assessed in a double-blind, placebo-controlled, crossover study.

13 healthy male and female subjects (24±5 years, 170.0±11.8 cm, 72.9±19.3 kg, 24.8±3.7 kg/m$^2$) were randomly assigned to consume 400 mg of the extract composition or placebo (PLA). Subjects completed four cognitive function tests (go no-go test, psychomotor vigilance task test, the Berg-Washington card sorting task, and the Sternberg task test), and then ingested a capsule of ashwagandha extract or PLA with 8 ounces of water. Participants repeated cognitive function tests 1, 2, 3, 4, 5, and 6 hours after ingestion of the supplement. After 7 days participants then repeated the experiment while consuming the alternative treatments. Data were analyzed by a General Linear Model multivariate and univariate analyses with repeated measures using body weight as a covariate.

Acute supplementation with *Withania somnifera* extract significantly increased short-term/working memory in. Acute supplementation with *Withania somnifera* extract also resulted in sustained attention (maintained reaction times, prevention of mental fatigue) in the Vigilance Task Test. In contrast, placebo showed significantly reduced reactions times. Further, acute supplementation with *Withania somnifera* extract resulted in faster response times to correctly respond compared to PLA (shows less metal fatigue) in the go/no-go test.

The invention claimed is:

1. A *Withania somnifera* extract composition comprising: between 2% (w/w) and 11% (w/w) of withaferin A; between 0.02% (w/w) and 0.2% (w/w) of withanolide A; between 0.05% (w/w) and 0.4% (w/w) of withanoside IV; and between 0.5% (w/w) and 4% (w/w) of withanoside V.

2. A nutraceutical composition comprising the extract composition according to claim 1 and one or more nutraceutically acceptable excipients.

3. The nutraceutical composition according to claim 2, wherein the composition additionally comprises one or more additional active ingredients.

4. The nutraceutical composition according to claim 2, wherein the composition is a tablet or capsule.

5. The nutraceutical composition according to claim 2, wherein the composition is a food or beverage comprising: water, milk, coffee, tea, juice, protein shake, energy drink, yoghurt, cereal or chocolate bar.

6. A food, food product, food additive or dietary supplement comprising the nutraceutical composition according to claim 2.

7. A method of improving or increasing one or more of the following conditions: mood, self-confidence, relaxation, wakefulness, mental alertness, focus, attention, mental energy, physical energy, natural energy, concentration, reasoning, motivation, stamina, strength, workout output, mobility, athletic speed, reaction time, athletic endurance, alertness, decision making, memory, cognitive performance, verbal fluency, sensuous perception, sexual desire and well-being; or reducing of one or more of the following conditions: appetite, boredom, anxiety and fatigue, said method comprising administering to a subject the nutraceutical composition according to claim 2.

8. A pharmaceutical composition comprising the composition according to claim 1, and one or more pharmaceutically acceptable excipients.

9. The pharmaceutical composition according to claim 8, wherein the composition is further in combination with one or more therapeutic agents.

10. A method for the treatment of one or more of the following conditions: attention deficit hyperactivity disorder (ADHD), and stress, said method comprising administering to a subject in need thereof the pharmaceutical composition according to claim 8.

11. A process for preparing the composition of claim 1, wherein the process comprises the steps of:
(a) drying *Withania somnifera* roots and/or leaves;
(b) crushing the dried root and/or leaves obtained in step (a) to obtain a dry powder;
(c) extracting the dry powder obtained in step (b) with an aqueous alcohol solvent followed by filtration to obtain a supernatant and residue;
(d) subjecting the supernatant obtained in step (c) to distillation to obtain a crude extract;
(e) purifying the crude extract obtained in step (d), thereby obtaining a first extract;
(f) subjecting the residue obtained in step (c) to hot water extraction followed by filtration and collection of a second supernatant to obtain a second extract; and
(g) combining the first and second extracts obtained in steps (e) and (f).

12. The process of claim 11 wherein:
the combined extracts of step (g) are spray dried to obtain an extract powder; and/or the drying temperature of step (a) is between 35 and 75° C.; and/or the aqueous alcohol solvent is ethyl alcohol; and/or the temperature of the aqueous alcohol solvent is between 5° and 60° C.; and/or the purification of step (e) is performed by any one of (i) solvent extraction, (ii) adsorbent resin treatment, or (iii) precipitation; and/or the hot water extraction is performed at a temperature of between 65 and 75° C.

13. The process of claim 12, wherein the purification of step (e) is performed by any one of (i) solvent extraction wherein the solvent is an ethyl acetate/ethyl alcohol mixture, (ii) adsorbent resin treatment wherein the resin is HP20 resin and wherein the extract is eluted with ethyl alcohol, or (iii) precipitation wherein the precipitant is sodium chloride.

* * * * *